(12) United States Patent
Bouhnik et al.

(10) Patent No.: US 8,957,384 B2
(45) Date of Patent: Feb. 17, 2015

(54) GAMMA RAY DETECTOR LINEARITY CALIBRATION

(75) Inventors: Jean-Paul Bouhnik, Zichron Yaakov (IL); Yaron Hefetz, Herzeliya (IL)

(73) Assignee: General Electric Company, Schenectady, NY (US)

(*) Notice: Subject to any disclaimer, the term of this patent is extended or adjusted under 35 U.S.C. 154(b) by 28 days.

(21) Appl. No.: 13/019,590

(22) Filed: Feb. 2, 2011

(65) Prior Publication Data
US 2012/0193541 A1    Aug. 2, 2012

(51) Int. Cl.
*G01T 1/20* (2006.01)
*G01T 1/164* (2006.01)
*G01T 7/00* (2006.01)

(52) U.S. Cl.
CPC .............. *G01T 1/1644* (2013.01); *G01T 7/005* (2013.01)
USPC .......................................................... 250/362

(58) Field of Classification Search
CPC ........... G01T 1/20; G01T 1/1642; G01T 7/00; G01T 1/202; G01T 7/005
USPC .......................................................... 250/362
See application file for complete search history.

(56) References Cited

U.S. PATENT DOCUMENTS

| | | | | |
|---|---|---|---|---|
| 3,851,177 | A * | 11/1974 | Van Dijk et al. | 250/366 |
| 5,345,082 | A * | 9/1994 | Engdahl et al. | 250/363.07 |
| 6,621,084 | B1 | 9/2003 | Wainer et al. | |
| 7,291,844 | B2 * | 11/2007 | Yahata et al. | 250/370.11 |
| 7,692,156 | B1 * | 4/2010 | Nagarkar | 250/370.11 |
| 2005/0167605 | A1 * | 8/2005 | Juni | 250/370.11 |
| 2005/0236577 | A1 * | 10/2005 | Katagiri | 250/390.11 |
| 2010/0012846 | A1 * | 1/2010 | Wang | 250/362 |
| 2010/0065724 | A1 * | 3/2010 | Hughes et al. | 250/216 |

* cited by examiner

*Primary Examiner* — Marcus Taningco
(74) *Attorney, Agent, or Firm* — Fletcher Yoder, P.C.

(57) ABSTRACT

A gamma ray detector having a scintillator with segments allows for a linearity calibration of the gamma ray detector without the use of a linearity phantom. The segments in the scintillator are configured to channel output radiation received by the gamma ray detector to loci identifiable in image data generated by photomultiplier tubes. The non-linearity in the detector system may be characterized, and a correction map may be generated, based upon the identifiable loci.

20 Claims, 4 Drawing Sheets

GAMMA RAY DETECTOR LINEARITY CALIBRATION

BACKGROUND OF THE INVENTION

The subject matter disclosed herein relates to gamma ray detection, and, more particularly, to a technique for correcting non-linearity in a gamma ray detector.

A wide range of imaging techniques are known and currently in use, particularly for medical diagnostic applications. Certain of these techniques, commonly referred to as nuclear imaging, rely on detection of gamma rays during the radioactive decay of a radioisotope (or radionuclide), commonly administered in the form of a radiopharmaceutical agent that can be carried, and in some cases, bound to particular tissues of interest. A gamma ray detector detects the emissions via a gamma camera that typically includes a collimator, a scintillator, and a series of photomultiplier tubes. The collimator allows only emissions in a particular direction to enter into the scintillator. The scintillator converts the gamma radiation into lower energy ultraviolet photons that impact regions (pixels) of the photomultiplier tubes. These, in turn, generate image data related to the quantity of radiation impacting the individual regions. Image reconstruction techniques, such as backprojection, may then be used to construct images of internal structures of the subject based upon this image data.

One challenge in the use of gamma cameras is that they typically do not have a linear spatial response. Consequently, a calibration process is required to determine a necessary linearity correction for use in processing data collected by the cameras. The calibration process is done both during production of a gamma camera and during gamma camera maintenance. In general, the calibration process may be completed with the use of a linearity phantom, which captures gamma rays passing through its many apertures. The coordinates of the apertures are then used to determine the non-linearity of the gamma camera and generate the appropriate linearity correction map. However, linearity phantoms may be heavy, expensive, difficult to acquire and logistically cumbersome to use. Moreover, such calibration procedures typically require a visit by a skilled technician, and may be done at relatively extended intervals during regular or special system maintenance. Typically, a linearity phantom is placed directly on the detector. Thus, the collimator may need to be removed from the detector prior to the installation of the phantom. Collimator removal and replacement (in contrast to collimator exchange) is a non-standard and cumbersome operation that may require tools and skills beyond the capacity of hospital technicians.

BRIEF DESCRIPTION OF THE INVENTION

In one embodiment, a gamma ray detector system includes a scintillator configured to receive gamma radiation and to output lower energy radiation, where the scintillator has a plurality of segments configured to channel the output radiation. The gamma ray detector system further includes an intermediate layer disposed adjacent to the scintillator and a plurality of photomultipliers disposed adjacent to the intermediate layer. The plurality of photomultipliers is configured to receive the channeled output radiation and to convert the radiation into image data. The segments in the scintillator channel output radiation to loci detectable in the image data that characterize non-linearity in the detector system.

In another embodiment, a method for processing gamma ray detector data includes receiving output radiation in a detector system that has a scintillator configured to receive gamma radiation and to output lower energy radiation. The scintillator has a plurality of segments configured to channel the output radiation. The detector system also has an intermediate layer disposed adjacent to the scintillator and a plurality of photomultipliers disposed adjacent to the intermediate layer. The plurality of photomultipliers is configured to receive the channeled output radiation and to convert the radiation into image data. The method also includes, based upon the image data, identifying loci detectable in the image data resulting from the segments. The method further includes generating a non-linearity map of the detector system based upon the identifiable loci.

In a further embodiment, a gamma ray detector system includes a scintillator configured to receive gamma radiation and to output lower energy radiation. The scintillator includes a plurality of segments configured to channel the output radiation.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
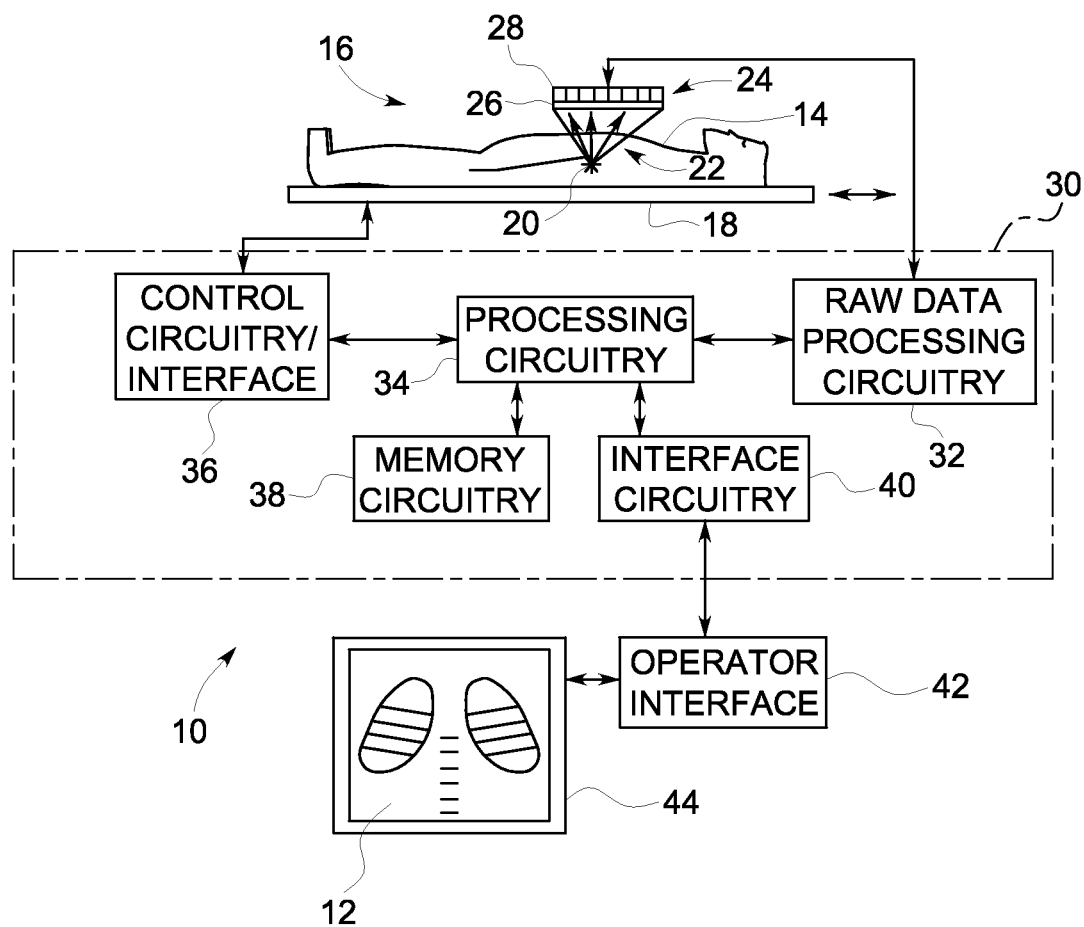
FIG. 1 is a diagrammatic representation of an exemplary gamma ray imaging system incorporating aspects of the present techniques.

A diagrammatic representation of an exemplary gamma ray imaging system is shown in FIG. 1. The system, designated generally by the reference numeral 10, is designed to produce useful images 12 of a subject 14. The subject is positioned in a scanner, designated by reference numeral 16 in which a patient support 18 is positioned. The support may be movable within the scanner to allow for imaging of different tissues or anatomies of interest within subject. Prior to image data collection, a radioisotope, such as a radiopharmaceutical substance (sometimes referred to as a radiotracer), is administered to the patient, and may be bound or taken up by particular tissues or organs. Typical radioisotopes include various radioactive forms of elements, although many in gamma ray imaging are based upon an isotope of technetium ($^{99}$Tc) that emits gamma radiation 22 during decay. Various additional substances may be selectively combined with such radioisotopes to target specific areas or tissues of the body.

Gamma radiation 22 emitted by the radioisotope is detected by a digital detector or gamma camera 24. Gamma cameras 24 may be used for various radionuclide imaging techniques including single proton emission computed tomography (SPECT) and positron emission tomography (PET). Although illustrated in the figure as a planar device positioned above the patient, in practice the camera 24 may be positioned below the patient, both above and below the patient, and may wrap at least partially around the patient. In general, the gamma camera 24 may comprise one or more collimators and a scintillator, together represented generally as reference numeral 26. The collimator allows gamma radiation emitted only in certain directions (typically perpendicular to the scintillator) to impact the scintillator. The scintillator, which is typically made of a crystalline material, such as sodium iodide (NaI), converts the received gamma radiation to lower energy light energy (e.g., in an ultraviolet range). Photomultiplier tubes 28 then receive this light and generate image data corresponding to photons impacting specific discrete picture element (pixel) regions.

The gamma camera is coupled to system control and processing circuitry 30. This circuitry may include a number of physical and functional components that cooperate to allow the collection and processing of image data to create the desired images. For example, the circuitry may include raw data processing circuitry 32 that initially receives the data from the gamma camera, and that may perform various filtering, value adjustments, and so forth. Processing circuitry 34 allows for the overall control of the imaging system, and for manipulation of image data. The processing circuitry 34 may also perform calibration functions, correction functions, and so forth on the data. The processing circuitry 34 may also perform image reconstruction functions, such as based on known algorithms (e.g., backprojection). Such functions may also be performed in post-processing on local or remote equipment (not shown). The processing circuitry may interact with control circuitry/interface 36 that allows for control of the scanner and its components, including the patient support, camera, and so forth. Moreover, the processing circuitry 34 will be supported by various circuits, such as memory circuitry 38 that may be used to store image data, calibration or correction values, routines performed by the processing circuitry, and so forth. Finally, the processing circuitry may interact with interface circuitry 40 designed to support an operator interface 42. The operator interface allows for imaging sequences to be commanded, scanner and system settings to be viewed and adjusted, images to be viewed, and so forth. In the illustrated embodiment, the operator interface includes a monitor 44 on which reconstructed images 12 may be viewed.

In an institutional setting, the imaging system 10 may be coupled to one of more networks to allow for the transfer of system data to and from the imaging system, as well as to permit transmission and storage of image data and processed images. For example, a local area networks, wide area networks, wireless networks, and so forth may allow for storage of image data on radiology department information systems or on hospital information systems. Such network connections further allow for transmission of image data to remote post-processing systems, physician offices, and so forth.

Figure 2:
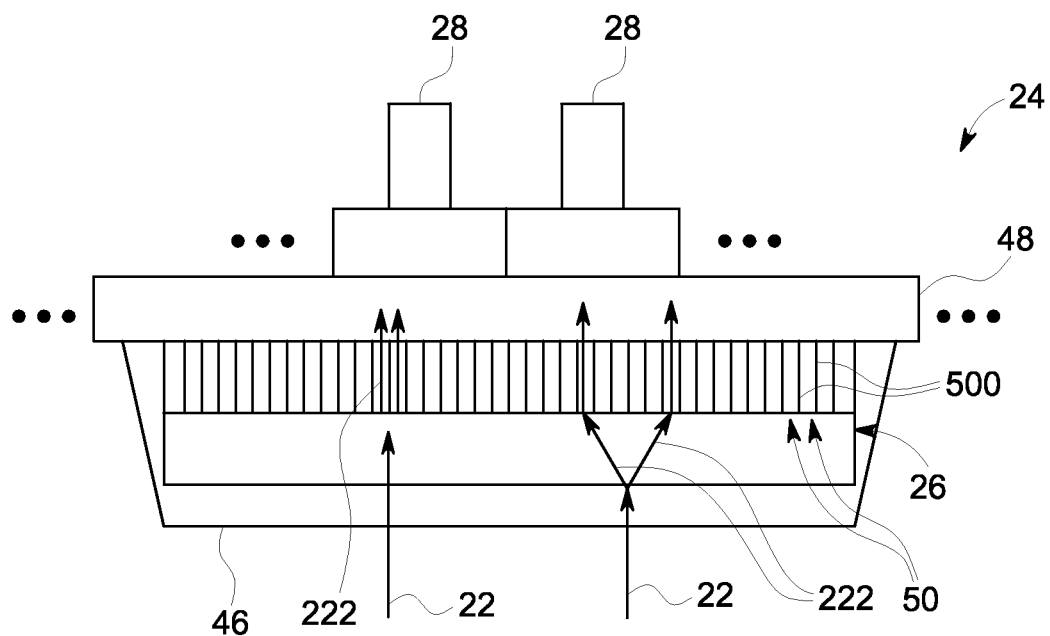
FIG. 2 is a cross-sectional side view of an exemplary gamma camera in accordance with aspects of the present techniques.

FIG. 2 is cross-sectional side view of an exemplary gamma camera 24 having a scintillator 26 and a plurality of photomultiplier tubes 28. As discussed above, the gamma camera 24 may be positioned above or below the patient, both above and below the patient, rotate about the patient, or may wrap at least partially around the patient. Furthermore, while the illustrated embodiment shows two photomultiplier tubes 28, in practice the gamma camera 24 may include numerous photomultiplier tubes 28 in a two dimensional array. For example, in certain embodiments, the gamma camera 24 may include between 37 and 91 photomultiplier tubes 28. The photomultiplier tubes 28 may comprise a variety of configurations. For example, in some embodiments, the photomultiplier tubes 28 may be arranged in a hexagonal pattern.

As shown in the illustrated embodiment, the gamma camera 24 further includes a scintillator enclosure 46 at least partially surrounding the scintillator crystal 26. In certain embodiments, the scintillator enclosure may be made from aluminum and glass. As previously mentioned, the scintillator crystal 26 is typically made of a crystalline material, such as sodium iodide (NaI), and converts the received gamma radiation to lower energy light energy. As will be appreciated, the thickness of the scintillator crystal 26 may vary for different imaging applications. For example, in certain low energy (e.g., ~140 keV) applications, the scintillator crystal 26 may be approximately 0.375" thick. In higher energy (e.g., ~300 keV) applications, the scintillator crystal 26 may be approximately 0.75" to 1.0" thick. In even higher energy (e.g., ~511 keV) applications, the scintillator crystal 26 may be equal to or greater than 1.0" thick. The gamma camera 24 further includes an intermediate layer 48 disposed adjacent to the scintillator crystal 26. The intermediate layer 48 may be made from glass or a combination of glass and transparent plastic, and may be approximately 0.5" thick. Additionally, the intermediate layer 48 may be secured to the scintillator crystal 26 by an adhesive or glue, such as silicon rubber. As shown, the photomultiplier tubes 28 are disposed adjacent to the intermediate layer 48.

Gamma radiation 22 passes through the scintillator crystal 26. As mentioned above, the scintillator crystal 26 converts the gamma radiation 22 into light photons 222. The light photons 222 pass through the scintillator crystal 26 and the intermediate layer 48 and are received by the photomultiplier tubes 28. As mentioned above, the array of photomultiplier tubes 38 may generate image data based on the light photons 222 received from the scintillator crystal 26. More particularly, known algorithms, such as the Anger algorithm, may be used to generate image data by estimating scintillation point coordinates. However, as will be appreciated, in imaging applications using thicker scintillation crystals 26, the light photons 222 created by a scintillation event within the scintillation crystal 26 may spread extensively before the light photons 222 reach the photomultiplier tubes 28. For example, a portion of the light photons 222 created by a scintillation event may pass towards nearby photomultiplier tubes 28, a portion of the light photons 222 may pass towards more distant photomultiplier tubes 28, and a portion of the light photons 222 may pass towards the source of the gamma radiation 22 (i.e., away from the photomultiplier tubes 28). Consequently, the usefulness of the information output from the photomultiplier tubes 28 may decrease, and, thus, the accuracy of algorithm estimations may decrease. This problem may be magnified in imaging applications using thicker scintillation crystals and lower energies where the penetrating power of the gamma radiation 22 is reduced.

To address the issue of image distortions caused by light spread in the scintillator crystal 26, a non-linearity correction map may be generated to properly calibrate the gamma camera 24. As discussed in further detail below, a non-linearity correction map may be created by passing various levels of gamma radiation 22 through a gamma camera 24 having a scintillator crystal 26 with segments 50. Specifically, the scintillator crystal 26 includes segments 50 that are configured to at least partially channel the light photons 222 generated by the gamma radiation 22 received by the scintillator crystal 26. As shown in FIG. 2, the gamma radiation 22 enters the scintillator crystal 26 where it interacts with the scintillator crystal 26, creating a large number of light photons 222 which spread within the scintillator crystal 26. The light photons 222 eventually arrive and are detected by the photomultiplier tubes 28. The light photons 222 may reflect off the borders of the segments 50 and continue to travel through the scintillator crystal 26 towards the photomultiplier tubes 28, as discussed in greater detail below.

In the illustrated embodiment, the segments 50 are formed by grooves 500 on the side of the scintillator crystal 26 that is disposed adjacent to the intermediate layer 48. In certain embodiments, the depth of the segments 50 may be approximately 25% of the depth of the scintillator crystal 26. For example, the segments 50 may be approximately 0.25" deep in a scintillator crystal 26 that is approximately 1.0" thick. Moreover, the grooves 500 created to form the segments 50 may be filled with an adhesive such as glue or silicon rubber. As will be appreciated, the same adhesive used to secure the scintillator crystal 26 to the intermediate layer 48 may be used to fill the grooves 500 of the segments 50. In other embodiments, the segments 50 may be created by grooves 500 formed on the side of the scintillator crystal 26 that initially receives the gamma radiation 22 from the subject 14, or the segments 50 may be formed by grooves 500 that pass completely through the scintillator crystal 26. As discussed in further detail below, the segments 50 may be formed to create a variety of grid configurations with different pitches and geometries.

Figure 3:
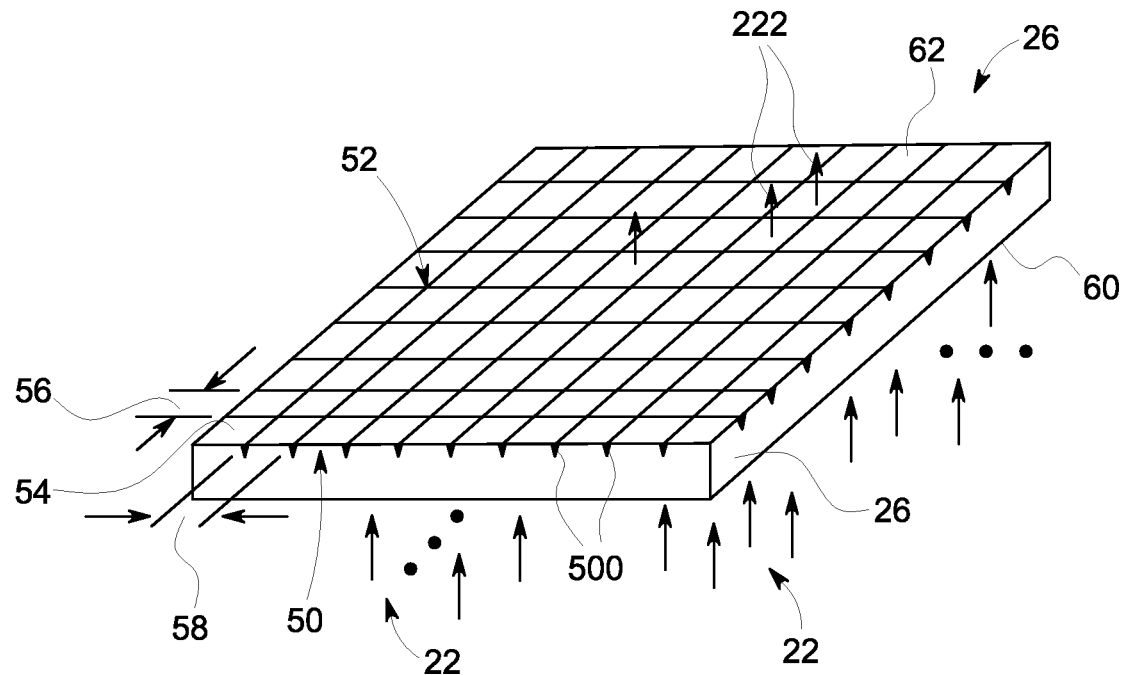
FIG. 3 is a perspective view of an exemplary scintillator including segments configured to channel output radiation in accordance with aspects of the present techniques.

FIG. 3 is a perspective view of an exemplary scintillator crystal 26. More specifically, the illustrated embodiment includes a scintillator crystal 26 having segments 50 that form a square grid pattern 52. In other embodiments, the segments 50 may be configured to form a triangular or rhombical grid pattern. As shown, the grid 52, formed by the segments 50, defines a plurality of columns 54 on the scintillator crystal 26. Each column 54 formed by the segments 50 has a Y-direction pitch 56 and an X-direction pitch 58. The segments 50 may be formed such that the Y-direction pitch 56 is constant for all columns 54 in the Cartesian grid 52. Similarly, the segments 50 may be formed such that the X-direction pitch 58 is constant for all columns 54 formed in the Cartesian grid 52. In certain embodiments, the Y-direction pitch 56 and the X-direction pitch 58 may be equal. For example, the Y-direction pitch 56 and the X-direction pitch 58 may both be equal to 0.25".

As shown in the illustrated embodiment, gamma radiation 22 may enter the scintillator crystal 26 through a first side 60. Thereafter, the light energy 222 created by the interaction between the scintillator crystal 26 and the gamma radiation 22 may exit the scintillator crystal 26 through a second side 62. As discussed in further detail below, a constant Y-direction pitch 56 and a constant X-direction pitch 58 may cause the light energy 222 created from the gamma radiation 22 to experience reflection effects around the segments 50 of the scintillator crystal 26 such that the light energy 222 passes mainly through the center of the columns 54. Thereafter, the light energy 222 will be collected by the photomultipliers 28. Subsequently, the data generated by the photomultiplier tubes 28 will represent the pattern of the columns 54 in the grid 52. This pattern may then be used to create the non-linearity correction map.

Figure 4:
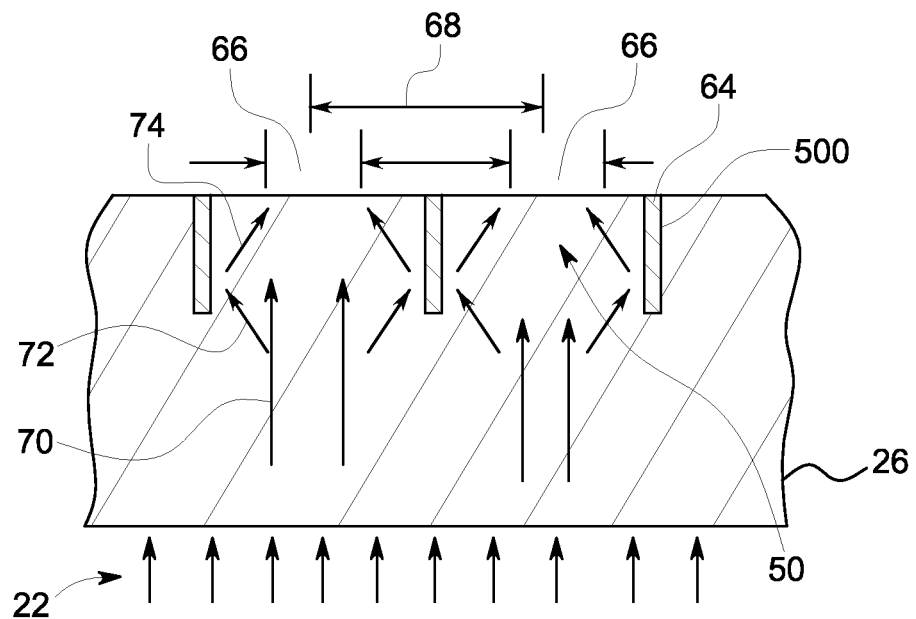
FIG. 4 is a cross-sectional side view of an exemplary scintillator including segments configured to channel output radiation in accordance with aspects of the present techniques.

FIG. 4 is a cross-sectional side view of a portion of a scintillator crystal 26 having multiple segments 50. As shown, the segments 50 are created by grooves 500 formed on one side of the scintillator crystal 26. More particularly, the segments 50 are created by grooves 500 formed on the side of the scintillator crystal 26 that is opposite the side of the scintillator crystal 26 that receives the gamma radiation 22. Further, in the illustrated embodiment, the depth of the segments 50 is less than 50% of the depth of the scintillator crystal 26. As previously mentioned, in alternative embodiments, the segments 50 may be formed on the side of the scintillator crystal 26 that receives the gamma radiation 22, or, alternatively, the segments 50 may be formed such that the segments 50 pass all the way through the scintillator crystal 26. In the illustrated embodiment, the grooves 500 that form the segments 50 are also filled with an adhesive 64. As discussed above, the adhesive 64 may be a glue such as silicon rubber.

The segments 50 are configured such that the segments 50 define a plurality of loci 66 having a pitch 68. In certain embodiments, the pitch 68 of the loci 66 may be constant. As will be appreciated, the constant pitch 68 of the loci 66 may be equal to the constant pitch of the segments 50. As mentioned above, the constant pitch and geometry of the segments 50 cause light energy 222 created from the gamma radiation 22 to be reflected and directed to pass mainly through the center of the columns 54 formed by the segments 50. In the illustrated embodiment, the respective centers of the columns 54 are identified by the loci 66. By way of example, a gamma ray may enter the scintillator crystal 26 in a direction 70. However, the light energy created from the gamma ray may not continue in the direction 70. Instead, the interaction between the gamma ray and the scintillator crystal 26 may cause light energy created by the interaction to travel in other directions. For example, a portion of the light energy may travel in a direction 72. The light energy may further contact and reflect off a boundary of a segment 50, causing the light energy to travel in a direction 74 towards the locus 66. As discussed above, such reflective effects may cause a large portion of the light energy created from the gamma radiation 22 to pass through the locus 66. As will be appreciated, the depth of the grooves 500 of the segments 50 may affect how much light energy is reflected off of the segments 50. For example, segments 50 having deeper grooves 500 may reflect more light energy towards the loci 66. Once the light energy passes through the locus 66, it will travel through the intermediate layer 48, and it will be received by the photomultipliers 28. The photomultipliers 28 may then generate image data corresponding to the light energy impacting the loci 66, which may be used to create a non-linearity correction map, as discussed below.

Figure 5:
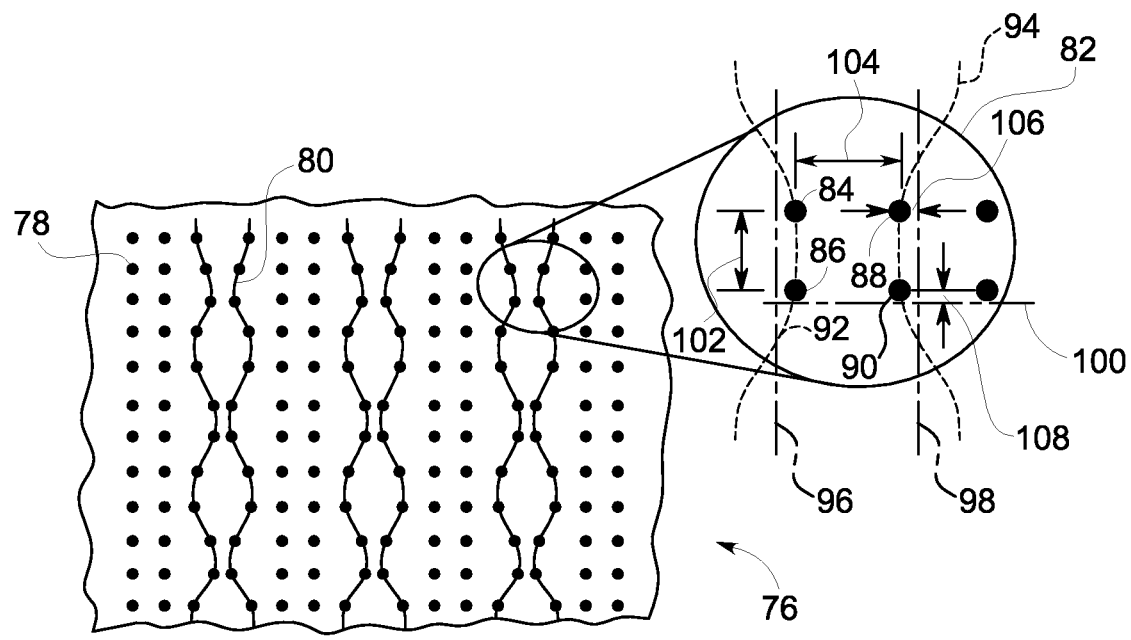
FIG. 5 is a diagram of exemplary image data that may be produced by an exemplary gamma ray imaging system to generate a non-linearity correction map incorporating aspects of the present techniques.

FIG. 5 is diagram of exemplary image data 76 that may be generated by applying the Anger algorithm on data from the array of photomultipliers 28 during a linearity calibration sequence using the scintillator crystal 26 shown in FIG. 3. As shown, the image data 76 includes many loci 78. As will be appreciated, based on the scintillator crystal 26 shown in FIG. 3, the image data 76 may be expected to display loci 78 in a Cartesian grid configuration with a Y-direction pitch 56 and an X-direction pitch 58. In other words, each locus 78 may correspond with the center of a column 54 in the scintillator crystal 26. However, due to the non-linear spatial response of the gamma camera 24, not all loci 78 may demonstrate the Cartesian grid 54, the Y-direction pitch 56, the X-direction pitch 58, or a combination thereof. Any variation between the expected location and the actual location of a locus 78 may be caused by distortion attributable to the non-linear spatial response of the gamma camera 24. As discussed in further detail below, the known actual position of a locus 78 may be used to generate a non-linearity correction. Furthermore, one or more curve-fit correction lines 80 may be generated between the loci 78. The curve-fit correction line 80 may help develop a non-linear correction map for gamma cameras 24 having different resolutions.

The enlarged portion 82 of FIG. 5 includes a first locus 84, a second locus 86, a third locus 88, and a fourth locus 90, each of which deviates from the location that each respective locus is expected to appear in the image data 76. As mentioned above, one or more curve-fit correction lines may be generated between a number of loci 78 for use in generating non-linear correction maps for gamma cameras 24 with different resolutions. For example, in the enlarged portion 82 of FIG. 5, a first curve-fit correction line 92 may be calculated that includes the first locus 84 and the second locus 86. In certain embodiments, the first curve-fit correction line 92 may be used to estimate the linear correction for a locus between the first locus 84 and the second locus 86 (not shown). Similarly, a second curve-fit correction line 94 may be calculated that includes the third locus 88 and the fourth locus 90.

As mentioned above, a non-linear correction map may be built by comparing the actual location of a locus with the expected location of that locus. For example, the expected location of the first locus 84 may be along a first line 96 in the Y-direction. Similarly, the expected location of the second locus 86 may be along the first line 96 in the Y-direction, and the respective expected locations of the third locus 88 and the fourth locus 90 may be along a second line 98 in the Y-direction. A non-linear correction may be calculated for each locus by measuring the deviation between the actual location and the expected location of the locus. For example, the deviation 106 in the X-direction may be determined to help calculate the non-linear correction for the third locus 88. For further example, the expected location of the fourth locus 90 may also be along a line 100 in the X-direction. As a result, a deviation 108 in the Y-direction may be determined to help calculate the non-linear correction for the fourth locus 90. As will be appreciated, calculations such as those described above may be completed for each locus 78 in the image data 76 that deviates from its respective expected location. The aggregate of the calculated deviations may then be used to form a non-linearity correction map for the gamma camera 24.

In addition to calculating a non-linear correction for the loci 78 by comparing the actual and expected locations for each locus 78, a non-linear correction may be calculated by comparing the actual pitch of two loci 78 with the expected pitch of the two loci 78. As discussed above, it is important to note that the pitch of the expected loci 66 may be identical to the pitch of the segments 50 in the scintillator crystal 26. For example, in the enlarged portion 82 of FIG. 5, the first locus 84 and the second locus 86 have an actual Y-direction pitch 102. The actual Y-direction pitch 102 may be compared to the constant Y-direction pitch 56 of the segments 50 in the scintillator crystal 26 (i.e., the expected Y-direction pitch of the first locus 84 and the second locus 86). The deviation between the actual Y-direction pitch 102 of the first locus 84 and the second locus 86 and the constant Y-direction pitch 56 of the segments 50 may be used to calculate a non-linear correction for the first locus 84 and the second locus 86. For further example, the first locus 84 and the third locus 88 have an actual X-direction pitch 104. Similar to the comparison described above, the deviation between the actual X-direction pitch 104 between the first locus 84 and the third locus 88 and the constant X-direction pitch 58 of the segments 50 in the scintillator crystal 26 (i.e., the expected X-direction pitch of the first locus 84 and the third locus 88) may be used to calculate a non-linear correction for the first locus 84 and the third locus 88. As will be appreciated, a non-linearity correction map may be generated using deviations between actual pitches and expected pitches between the loci 78 as well as using deviations between actual locations and expected locations of the loci 78.

Figure 6:
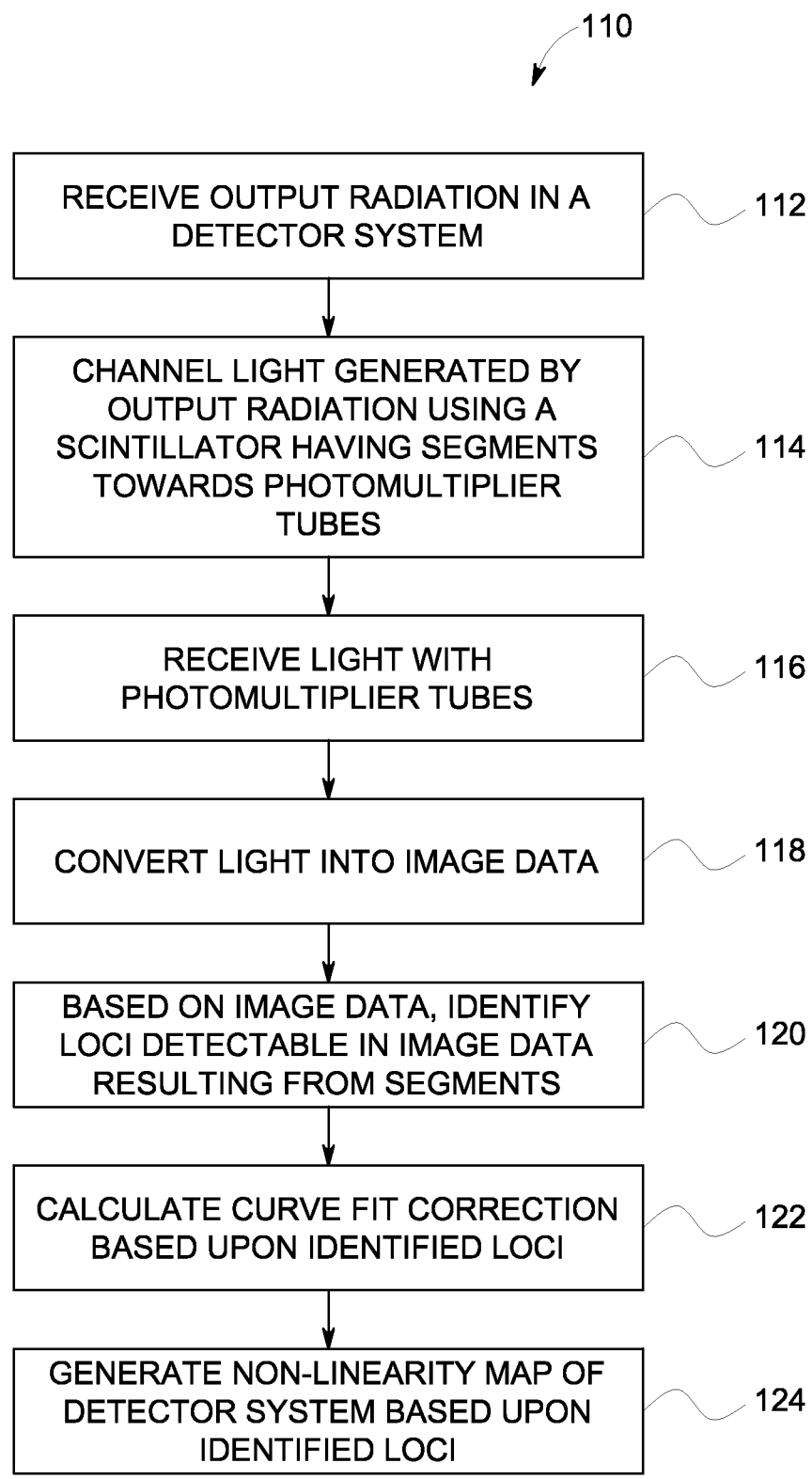
FIG. 6 is a method flow diagram of an exemplary method that may be utilized to generate a non-linearity correction map.

FIG. 6 is a flow chart illustrating an exemplary method 110 for processing gamma ray detector data to generate a non-linearity correction map. First, a detector system receives radiation, as indicated by reference numeral 112. Preferably, the radiation is gamma radiation substantially exposed to the entire front surface of the detector and substantially uniform. Such radiation may be produced by a small radioactive source held at a distance from the exposed face of the detector. Alternatively, a plate of radioactive material, for example as used routinely for uniformity testing of the camera, may be placed on the collimator attached to the detector. As described above, the detector system may be a gamma camera that receives gamma radiation emitted by a radioisotope administered to a patient. The detector system may include a scintillator having segments that channel light generated by the output radiation towards photomultiplier tubes, as indicated by reference numeral 114. The segments in the scintillator may comprise a variety of configurations and may direct the light to specific loci. Next, as indicated by reference numeral 116, the light may be received by the photomultiplier tubes. The photomultiplier tubes may then convert the light into useful image data, as indicated by reference numeral 118. Based on this image data, loci detectable in the image data resulting from the segments in the scintillator may be identified, as indicated by reference numeral 120. The identified loci may deviate from their expected locations due to the non-linear spatial response of the gamma camera or detector system. As a result, a curve-fit correction based on the identified loci may be calculated, as indicated by reference numeral 122. The calculated curve-fit correction may be used to determine a non-linear correction for detector systems of different resolutions. Finally, a non-linearity correction map of the detector system based upon the identified loci, as indicated by reference numeral 124. As discussed above, deviations between actual pitches and expected pitches between the loci as well as deviations between actual locations and expected locations of the loci may be used to generate the non-linearity correction map. The generated non-linearity correction map may be used to correct images acquired by the detector during clinical examination of patients with a radioactive isotope.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A gamma ray detector system comprising:
   a scintillator configured to receive gamma radiation and to output lower energy radiation, the scintillator comprising a plurality of segments configured to channel the output radiation, wherein the segments are defined by physical walls of uniform depth formed across the entire scintillator and are configured to channel the output radiation to loci detectable in image data that characterize non-linearity in the detector system;

an intermediate layer disposed adjacent to the scintillator; and a plurality of photomultipliers disposed adjacent to the intermediate layer and configured to receive the channeled output radiation and to convert the radiation into the image data.

2. The system of claim 1, wherein the physical walls are formed by grooves in the scintillator that extend to a depth less than the thickness of the scintillator.

3. The system of claim 2, wherein the grooves are filled with an adhesive.

4. The system of claim 2, wherein the grooves have a depth of between approximately 10% and 50% of the thickness of the scintillator.

5. The system of claim 2, wherein the grooves are formed in a side of the scintillator that faces the intermediate layer.

6. The system of claim 5, wherein the intermediate layer comprises a glass.

7. The system of claim 1, wherein the segments are formed in a grid-pattern.

8. A method for processing gamma ray detector data comprising:
receiving output radiation in a detector system that comprises a scintillator configured to receive gamma radiation and to output lower energy radiation, the scintillator comprising a plurality of segments of uniform depth formed across the entire scintillator and configured to channel the output radiation, an intermediate layer disposed adjacent to the scintillator, and a plurality of photomultipliers disposed adjacent to the intermediate layer and configured to receive the channeled output radiation and to convert the radiation into image data;
based upon the image data, identifying loci detectable in the image data resulting from the segments; and
generating a non-linearity map of the detector system based upon the identified loci.

9. The method of claim 8, wherein the non-linearity map is generated by comparing locations of the loci with known locations or pitch of the segments.

10. The method of claim 8, wherein the non-linearity map is generated by exposing the detector system to gamma radiation in a dedicated calibration sequence.

11. The method of claim 8, wherein the non-linearity map is generated based upon image data taken during a series of imaging sequences on subjects of interest.

12. The method of claim 11, wherein the subjects of interest are patients imaged for clinical studies.

13. The method of claim 8, wherein the non-linearity map characterizes two dimensional shift of each locus from an expected location for the respective locus.

14. The method of claim 8, wherein the non-linearity map is generated by exposing the detector system to a substantially uniform gamma radiation.

15. The method of claim 14, wherein the substantially uniform gamma radiation is produced by exposing the detector to a radioactive source placed at a distance from the face of the detector without using an absorbing mask.

16. The method of claim 14, wherein the substantially uniform gamma radiation is produced by exposing the detector to a radioactive plate placed on a collimator attached to the detector.

17. A gamma ray detector system comprising:
a scintillator configured to receive gamma radiation and to output lower energy radiation, the scintillator comprising a plurality of physical grooves of uniform depth formed across the entire scintillator configured to channel the lower energy radiation to identifiable loci, wherein the identifiable loci are detectable in image data and characterize non-linearity in the detector system.

18. The system of claim 17, wherein the scintillator has a thickness of approximately 0.75 to 1.0 inches.

19. The system of claim 17, comprising an intermediate layer disposed adjacent to the scintillator.

20. The system of claim 19, comprising a plurality of photomultipliers disposed adjacent to the intermediate layer, wherein the photomultipliers are configured to receive the channeled output radiation and to convert the radiation into image data.

* * * * *